US005893863A

United States Patent [19]
Yoon

[11] Patent Number: 5,893,863
[45] Date of Patent: Apr. 13, 1999

[54] SURGICAL INSTRUMENT WITH JAWS AND MOVABLE INTERNAL HOOK MEMBER FOR USE THEREOF

[76] Inventor: InBae Yoon, 2101 Highland Ridge Dr., Phoenix, Md. 21131

[21] Appl. No.: 08/847,188

[22] Filed: May 1, 1997

Related U.S. Application Data

[63] Continuation-in-part of application No. 08/376,186, Jan. 20, 1995, Pat. No. 5,665,100, which is a continuation-in-part of application No. 08/281,814, Jul. 28, 1994, abandoned, which is a continuation of application No. 08/073,193, Jun. 8, 1993, Pat. No. 5,334,209, which is a continuation of application No. 07/720,381, Jun. 25, 1991, Pat. No. 5,217,473, which is a division of application No. 07/446,555, Dec. 5, 1989, Pat. No. 5,026,379.

[51] Int. Cl.$^6$ ............................................. A61B 17/32
[52] U.S. Cl. .................. 606/170; 606/205; 606/139; 606/144
[58] Field of Search ........................ 606/151, 170, 606/142, 144, 139, 148, 149, 205, 207, 167

[56] References Cited

U.S. PATENT DOCUMENTS

| | | |
|---|---|---|
| 2,002,594 | 5/1935 | Wappler et al. |
| 2,004,559 | 6/1935 | Wappler et al. |
| 2,028,635 | 1/1936 | Wappler |
| 4,077,412 | 3/1978 | Moossun |
| 4,103,680 | 8/1978 | Yoon |
| 4,249,533 | 2/1981 | Komiya |
| 4,257,420 | 3/1981 | Terayama |
| 4,372,295 | 2/1983 | Heckele |
| 4,374,523 | 2/1983 | Yoon |
| 4,393,872 | 7/1983 | Reznik et al. |
| 4,471,766 | 9/1984 | Terayama |
| 4,557,255 | 12/1985 | Goodman |
| 4,598,699 | 7/1986 | Garren et al. |
| 4,788,966 | 12/1988 | Yoon |
| 4,869,268 | 9/1989 | Yoon |
| 4,966,583 | 10/1990 | Debbas |
| 5,025,778 | 6/1991 | Silverstein et al. |
| 5,037,433 | 8/1991 | Wilk et al. |
| 5,133,727 | 7/1992 | Bales et al. ............... 606/170 |
| 5,139,487 | 8/1992 | Baber |
| 5,147,373 | 9/1992 | Ferzli |
| 5,190,541 | 3/1993 | Abele et al. |
| 5,211,650 | 5/1993 | Noda |
| 5,217,460 | 6/1993 | Knoepfler |
| 5,226,908 | 7/1993 | Yoon |
| 5,234,443 | 8/1993 | Phan et al. |
| 5,261,917 | 11/1993 | Hasson et al. |
| 5,312,391 | 5/1994 | Wilk |
| 5,318,589 | 6/1994 | Lichtman |
| 5,320,627 | 6/1994 | Sorensen et al. ............ 606/128 |
| 5,324,254 | 6/1994 | Phillips |
| 5,336,231 | 8/1994 | Adair |
| 5,348,555 | 9/1994 | Zinnanti |
| 5,366,476 | 11/1994 | Noda |
| 5,373,854 | 12/1994 | Kolozsi ................... 128/749 |
| 5,398,670 | 3/1995 | Ortiz et al. |
| 5,403,332 | 4/1995 | Christoudias |
| 5,462,561 | 10/1995 | Voda |
| 5,462,562 | 10/1995 | Elkus |
| 5,476,505 | 12/1995 | Limon |
| 5,496,310 | 3/1996 | Exconde et al. |
| 5,538,008 | 7/1996 | Crowe |
| 5,542,949 | 8/1996 | Yoon |
| 5,549,623 | 8/1996 | Sharpe et al. |
| 5,562,102 | 10/1996 | Taylor |
| 5,569,241 | 10/1996 | Edwards |
| 5,578,007 | 11/1996 | Imran |
| 5,607,435 | 3/1997 | Sachdeva et al. |
| 5,611,813 | 3/1997 | Lichtman |
| 5,620,459 | 4/1997 | Lichtman |
| 5,735,849 | 4/1998 | Baden et al. ............... 606/51 |

*Primary Examiner*—Michael Buiz
*Assistant Examiner*—Daphna Shai

[57] ABSTRACT

A surgical instrument includes a forceps unit for being positioned within an anatomical cavity and inner member having a hook. The forceps unit includes a housing, an outer tubular member, an intermediate member, and a handle mechanism coupled with at least one of the intermediate and outer tubular members for creating relative movement between the intermediate and outer tubular members. The outer tubular member has a proximal end mounted in the housing and terminates distally at a distal end. The intermediate member has a tubular body disposed telescopically within the outer tubular member, a proximal end mounted in the housing and a distal end defining a pair of opposed jaws resiliently biased apart such that relative movement of the outer tubular member distal end over the jaws causes the jaws to close. The inner member includes a tubular member slidingly disposed at least partly within the intermediate member and carrying a hook for performing at least one of the functions of cutting, grasping, manipulating, dissecting, penetrating tissue, injecting fluids, creating suction, aspirating, irrigating, suturing, ligating, visualizing, illuminating and cauterizing, or the like.

30 Claims, 12 Drawing Sheets

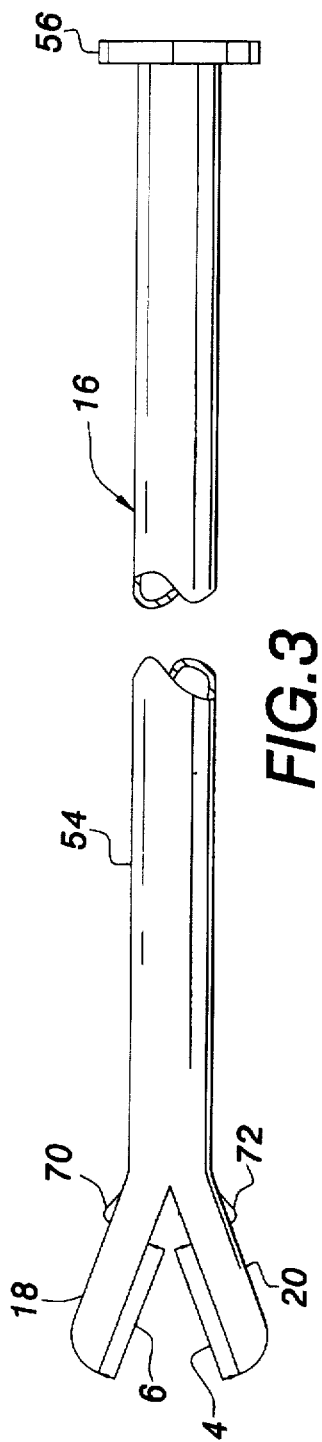
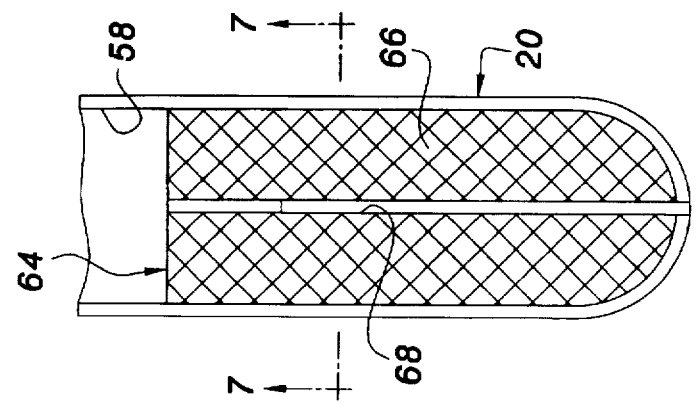
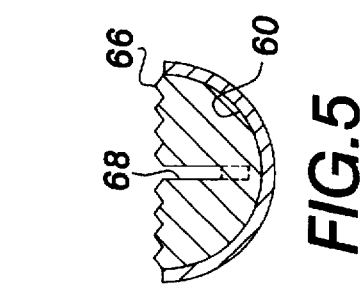
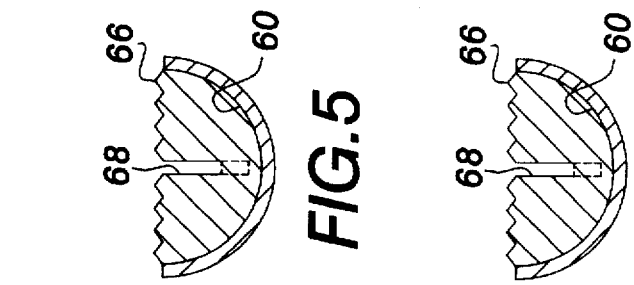
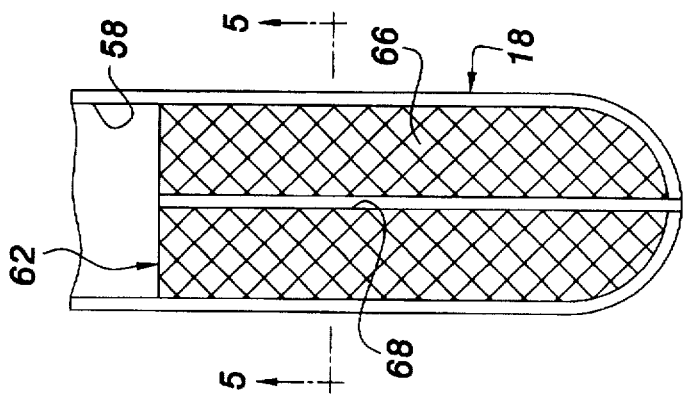

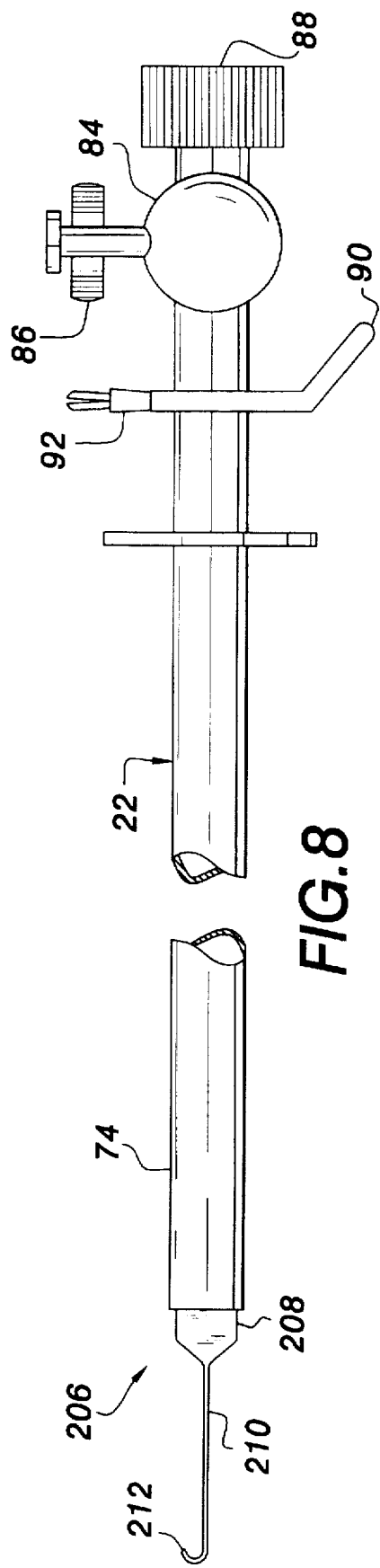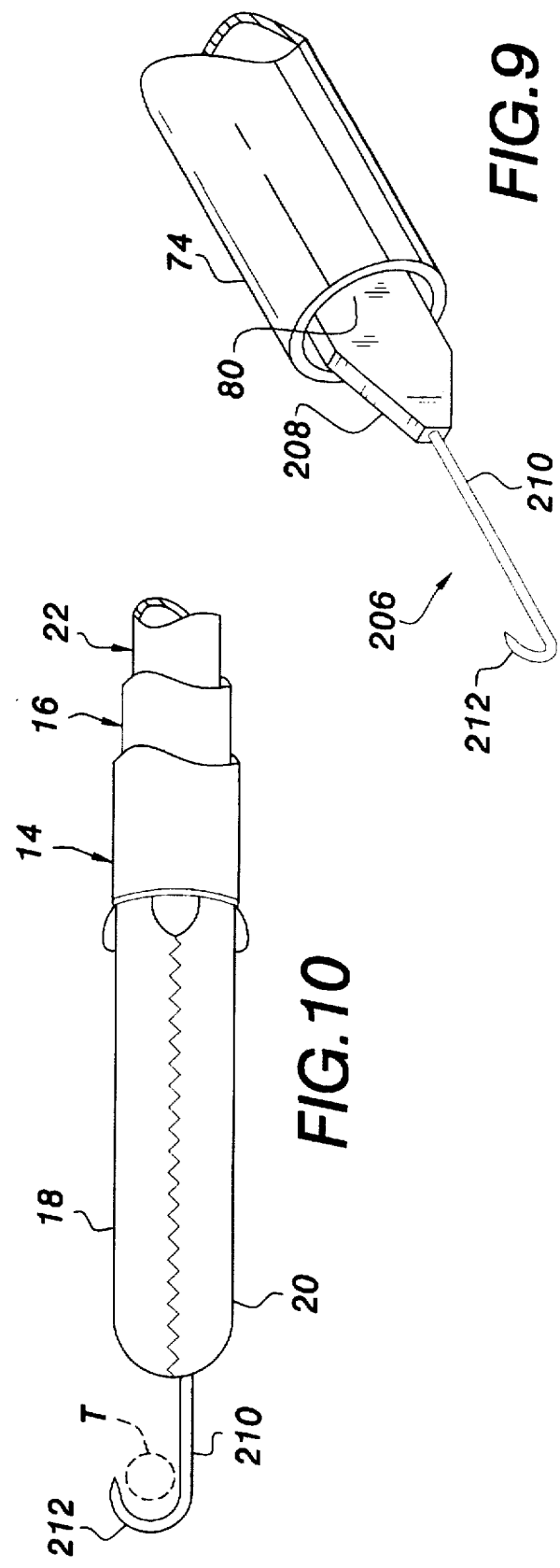

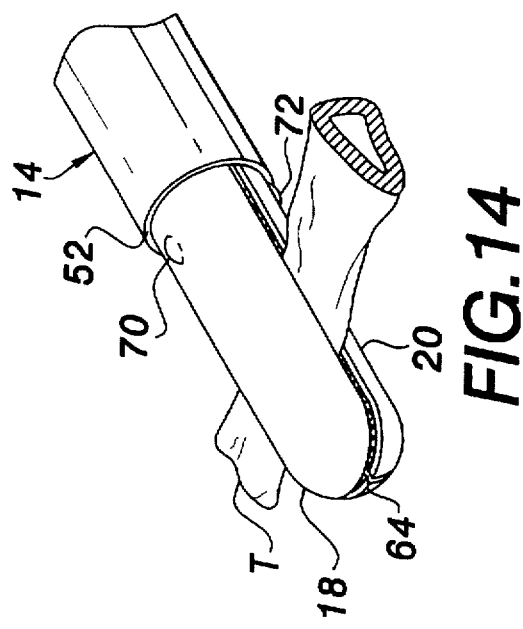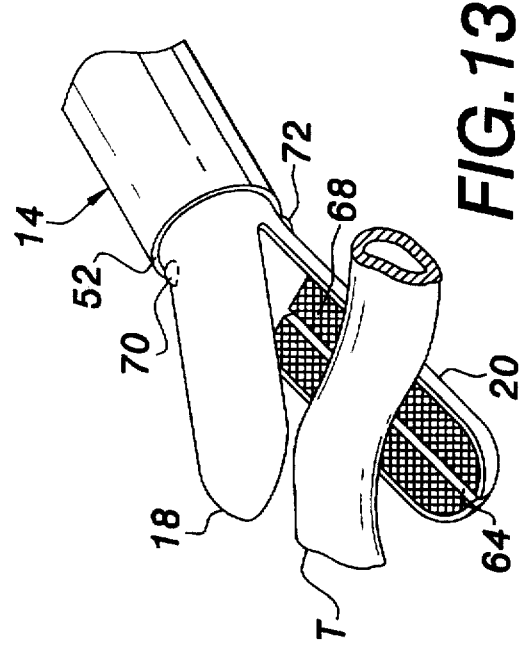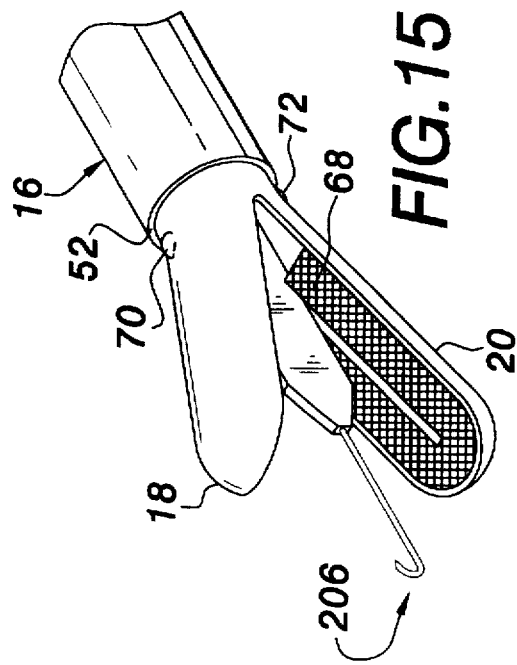
FIG. 14
FIG. 13
FIG. 15

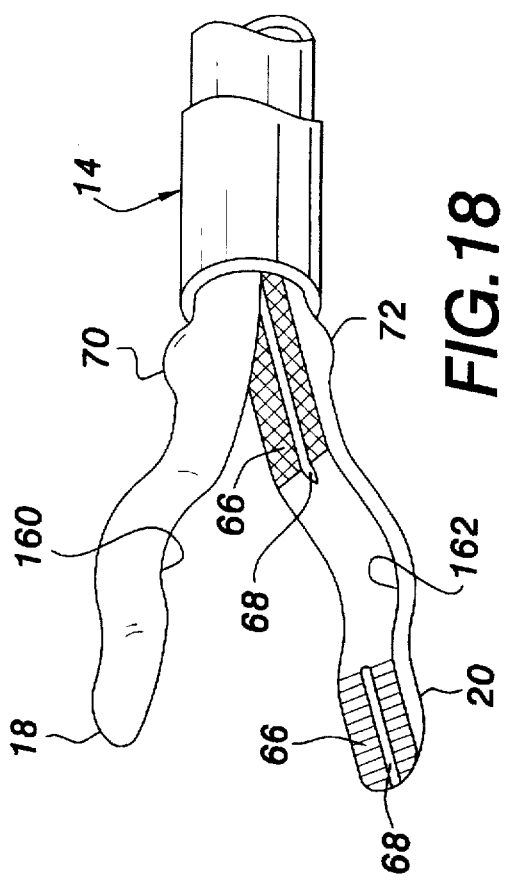
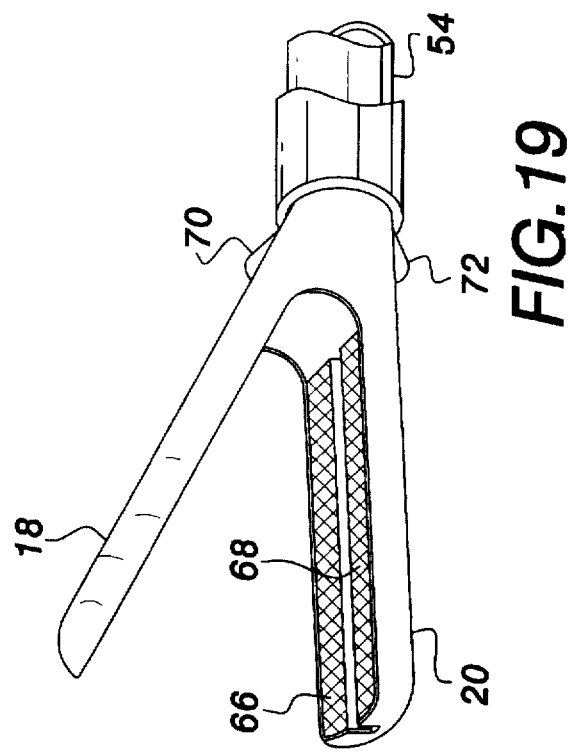

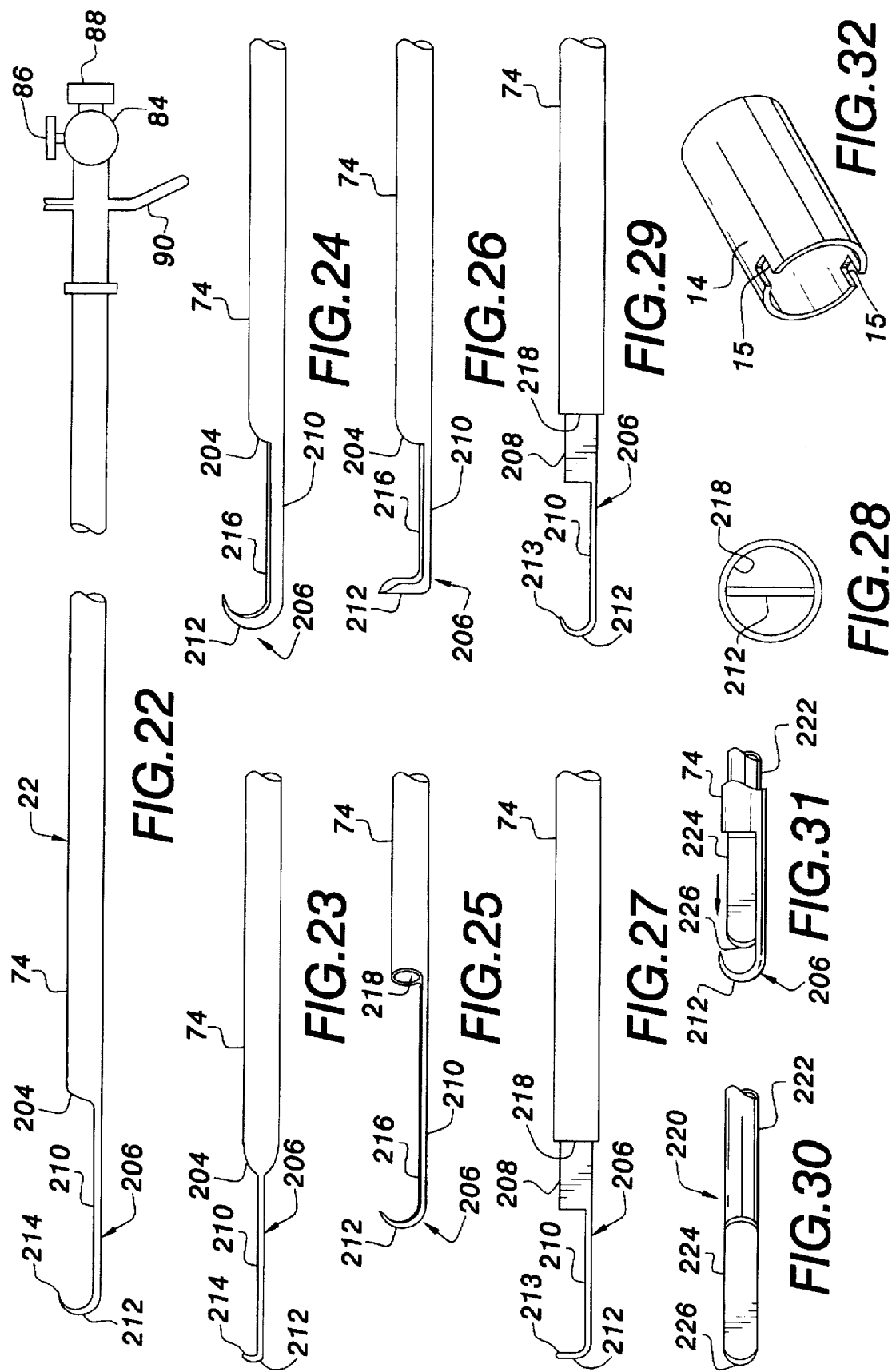

SURGICAL INSTRUMENT WITH JAWS AND MOVABLE INTERNAL HOOK MEMBER FOR USE THEREOF

CROSS-REFERENCE TO RELATED APPLICATIONS

This application is a continuation-in-part of Ser. No. 08/376,186, filed on Jan. 20, 1995 U.S. Pat. No. 5,665,100, which is a continuation-in-part of applicant's patent application Ser. No. 08/281,814, filed Jul. 28, 1994 now abandoned, which is a continuation of patent application Ser. No. 08/073,193, filed Jun. 8, 1993, now U.S. Pat. No. 5,334,209, which is a continuation of patent application Ser. No. 07/720,381, filed Jun. 25, 1991, now U.S. Pat. No. 5,217,473, which is a divisional of patent application Ser. No. 07/446,555, filed Dec. 5, 1989, now U.S. Pat. No. 5,026,379, the disclosures of which are incorporated herein by reference.

BACKGROUND OF THE INVENTION

1. Field of the Invention

The present invention relates generally to medical procedures and instruments and, more particularly, to a multifunctional instrument having jaws, a central channel, and a moveable internal hook member disposed in the channel for performing endoscopic procedures.

2. Discussion of the Related Art

Endoscopic and minimally invasive medical procedures, such as laparoscopy, have become widely accepted for surgery and diagnosis due to the associated advantages relating to reduced trauma and hospitalization time. The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, ligating appliers, forceps, cauteries and the like into the anatomical cavity.

Endoscopic procedures commonly involve performing a number of individual acts or functions within the anatomical cavity including grasping, cutting, coagulating, irrigating, aspirating, puncturing, injecting, dissecting, cauterizing, ligating, suturing, illuminating, visualizing and/or collecting specimens for biopsy. However, typical endoscopic instruments are capable of performing at most two of the above functions, requiring several incisions for placement of multiple portal sleeves to accommodate a suitable number of endoscopic instruments for performing the required functions or necessitating frequent withdrawal and replacement of individual endoscopic instruments through a single incision. While it is generally desirable to minimize the number of incisions created for performing a particular endoscopic procedure, substitution of instruments through a single incision can be time consuming, depending on the efficiency of the medical facility and staff, increasing the period of anesthetization for the patient. Additionally, internal bleeding can develop during the substitution of instruments thereby obscuring the field of view and requiring time consuming cleanup procedures to be performed.

A disadvantage of endoscopic instruments having articulated jaws, in particular, is that the jaws are typically mounted on pivots at the distal end of relatively long shafts requiring complicated and space-consuming linkages for converting the user's proximal movements into motion of the jaws and increasing the risk of fluid leaking through poorly sealed pivotal mounts.

SUMMARY OF THE INVENTION

Accordingly, it is a primary object of the present invention to overcome the above mentioned disadvantages of the prior art with an endoscopic instrument capable of performing multiple functions.

Another object of the present invention is to minimize the number of incisions required for performing an endoscopic procedure by performing multiple functions through a single incision with an endoscopic instrument having a forceps unit with jaws for performing grasping functions, a channel formed through the forceps unit, and a movable inner member having a hook for performing at least one of the functions of grasping, cutting, dissecting, aspirating, irrigating, penetrating, injecting, creating suction, hooking, manipulating and cauterizing through the forceps unit.

It is another object of the present invention to lock jaws of an endoscopic instrument together to ensure smooth entry of the endoscopic instrument through a portal sleeve and to prevent inadvertent snagging of anatomical tissue.

Some of the advantages of the present invention over the prior art are that the endoscopic instrument can perform multiple functions through a single incision thereby minimizing the number of incisions required to perform an endoscopic procedure, that use of an endoscopic instrument for picking-up and holding objects is simplified, that objects can be held without the need for exerting continuous hand or finger pressure, that single-handed operation of a forceps unit and a hook is facilitated, that conventional handle structures can be used to provide users with a familiar feel and to decrease adaptation time, that the instrument can be fabricated at low cost using simple mechanisms without complicated linkages, and that the instrument can be sterilized for reuse or disposable for single patient use as desired.

The present invention is generally characterized in an endoscopic instrument including a forceps unit for being positioned within an anatomical cavity, a channel formed through the forceps unit, and a moveable inner member disposed in the channel. The forceps unit includes a housing, an outer tubular member, an intermediate member, and a handle mechanism coupled with at least one of the intermediate and outer tubular members for creating relative movement therebetween. The outer tubular member has a proximal end mounted by the housing and terminates distally at a distal end. The intermediate member has a tubular body disposed telescopically within the outer tubular member, a proximal end mounted in the housing and a distal end defining a pair of opposed jaws resiliently biased apart such that relative movement of the outer tubular member distal end over the jaws causes the jaws to close. The movable inner member includes a shaft having a hook on a distal end removably disposed at least partly within the intermediate member for performing at least one of the functions of cutting, grasping, hooking, manipulating, dissecting, collecting tissue for biopsy, penetrating, injecting, creating suction, aspirating, irrigating and cauterizing.

A further aspect of the present invention is generally characterized in a method of performing an endoscopic procedure including the steps of introducing a tubular member with jaws through an opening in an anatomical cavity wall, grasping and manipulating anatomical tissue with the jaws, opening the jaws, advancing a moveable inner member having a hook distally through the tubular member, and performing a medical procedure involving at least one of the functions of cutting, grasping, dissecting, cauterizing, penetrating, injecting, hooking, manipulating, irrigating and aspirating with the inner member.

Yet another aspect of the present invention is generally characterized in a method of performing endoscopic procedures including the steps of introducing a tubular member with jaws through an opening in an anatomical cavity wall, advancing an inner member having a hook distally through the tubular member until the hook protrudes distally from the jaws and performing a medical procedure with the hook.

Other objects and advantages of the present invention will become apparent from the following description of the preferred embodiments taken in conjunction with the accompanying drawings, wherein like parts in each of the several figures are identified by the same reference characters.

BRIEF DESCRIPTION OF THE DRAWINGS

FIG. 3 illustrates the intermediate member;

FIG. 4 illustrates one of the jaws;

FIG. 5 is a cross-sectional view of the jaw of FIG. 4 taken along line 5—5;

FIG. 6 illustrates the other jaw;

FIG. 7 is a cross-sectional view of the jaw of FIG. 6 taken along line 7—7;

FIG. 8 illustrates the inner member;

FIG. 9 is a perspective view of a distal end of the inner member;

FIG. 10 illustrates a distal end of the preferred embodiment with the hook extended distally;

FIG. 13 illustrates the jaws before grasping tissue;

FIG. 14 illustrates the jaws grasping tissue;

FIG. 15 illustrates the jaws with the hook partially advanced distally;

FIGS. 18 and 19 illustrate alternative jaw configurations;

FIGS. 22–31 illustrate additional modified inner members; and

FIG. 32 illustrates the distal end of a modified outer member.

DESCRIPTION OF THE PREFERRED EMBODIMENT

The endoscopic instrument of the present invention can be utilized in any type of anatomical cavity; and, accordingly, while the instrument is described hereinafter for use with a portal sleeve in endoscopic procedures, such as laparoscopy, the instrument can be used with catheters and other small and large diameter cylindrical members providing access to small cavities, such as veins and arteries, as well as large cavities, such as the abdomen.

Figure 1:
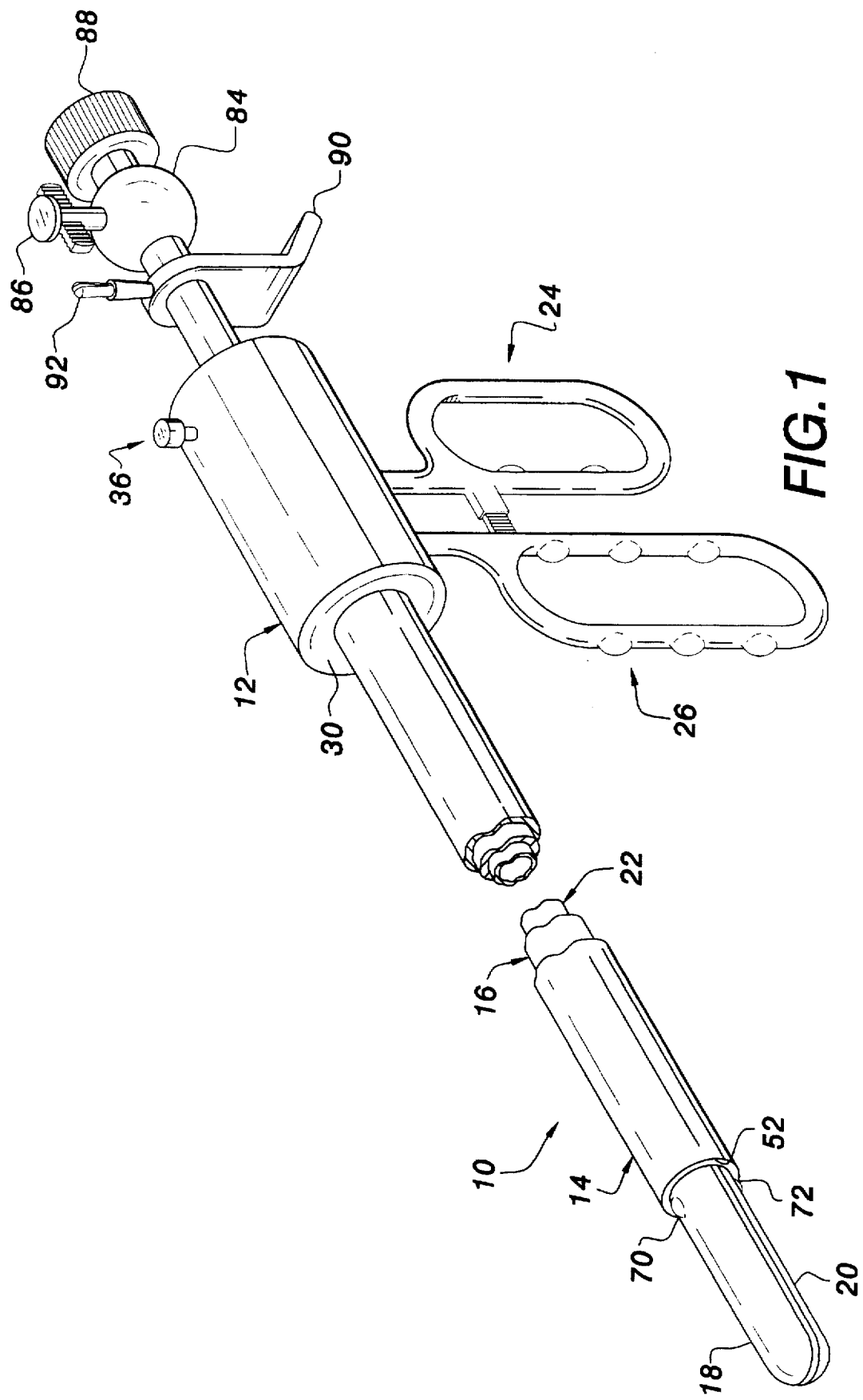
FIG. 1 is a perspective view, broken longitudinally, of an endoscopic instrument according to a preferred embodiment of the present invention.
Figure 2:
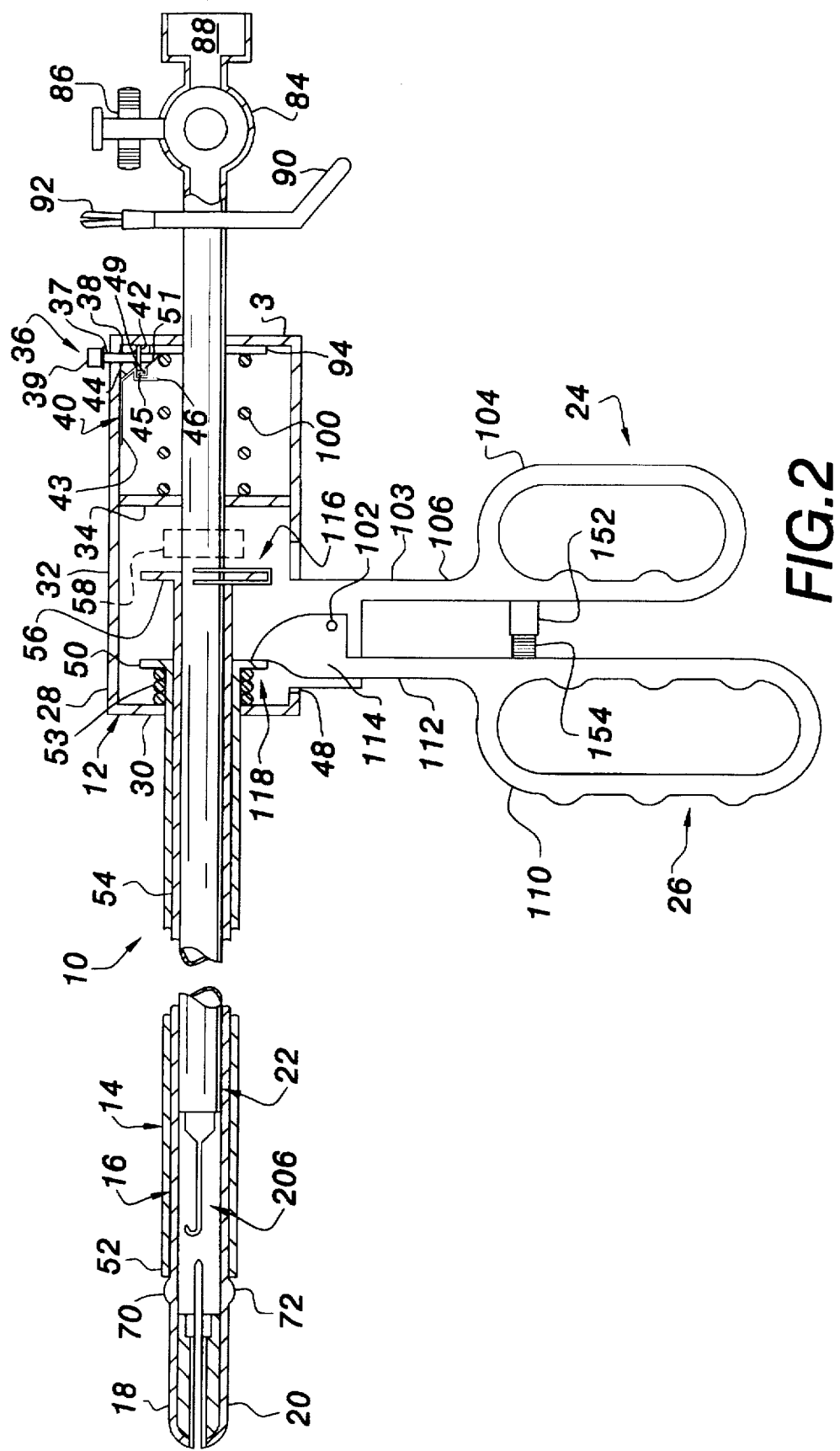
FIG. 2 is a sectional view of the preferred embodiment.

Endoscopic instrument 10 according to a first preferred embodiment of the present invention, as shown in FIGS. 1 and 2, includes housing 12, outer tubular member 14 extending distally from housing 12, intermediate tubular member 16 telescopically fined within outer tubular member 14 and having opposed jaws 18 and 20 on a distal end thereof, fixed handle 24 and moveable handle 26 extending from housing 12 at an angle relative to the longitudinal axis of the instrument, and inner member 22 which is at least partly telescopically fitted within intermediate member 16.

Housing 12 is generally tubular with cylindrical sidewall 28 and front and rear walls 30 and 31 closing opposite ends of the cylindrical sidewall 28. Intermediate wall 34 divides housing 12 into two compartments. Slotted opening 48 is formed in cylindrical sidewall 28 of housing 12 and extends longitudinally between front wall 30 and intermediate wall 34 to permit movable handle 26 to pass therethrough. Fixed handle 24 extends from plate 103 formed on housing 12 proximate slot 48. Plate 103 can be formed integrally with housing 12 or can be fixedly attached to housing 12 to be stationary relative thereto.

Outer member 14 is open at both ends and extends through an opening in front wall 30 to terminate proximally at transverse flange 50 disposed between front wall 30 and intermediate wall 34 of housing 12. Distal end 52 of outer tubular member 14 can be blunt as shown, tapered, beveled or chamfered as desired or have any other suitable distal configuration. Preferably, outer member 14 is made of a substantially cylindrical length of a substantially rigid material, such as stainless steel or other medically acceptable plastic or metal material.

Intermediate member 16 includes tubular body 54 telescopically fitted within the outer tubular member 14. Tubular body 54 terminates proximally at transverse flange 56 disposed within housing 12 between flange 50 and rear wall 31; and, as best seen in FIGS. 3–7 which show intermediate member 16 removed from outer member 14 for illustrative purposes, a distal end of tubular body 54 is split longitudinally to form integral one-piece jaws 18 and 20 that oppose one another. Jaws 18 and 20 are normally biased apart as shown and define opposed semicylindrical recesses 58 and 60 (see FIGS. 5 and 7) for carrying jaw inserts 62 and 64 respectively. Jaw inserts 62 and 64 can be permanently or removably secured within semicylindrical recesses 58 and 60 respectively using adhesives, detents, or any other suitable method of attachment or can be formed with jaws 18 and 20 as an integral one-piece construction. Each of inserts 58 and 60 defines a grasping surface or tread 66 suitable for grasping anatomical tissue or holding instruments such as a needle, and a longitudinal slot or groove 68 extending from a proximal end of insert 58 or 60 to a position proximally spaced from the distal end of insert 58 or 60. A repeated pattern of diamond-shaped protrusions is shown for tread 66. However, other surfaces such as those having parallel ribs or textured portions could be used. The length, width, and depth of each groove 68 will depend on the size of any hook carried by the inner member 22 as will be described in more detail below. Wedge-like cams 70 and 72 are formed on respective exterior surfaces of jaws 18 and 20 and are distally spaced from outer member distal end 52 when jaws 18 and 20 are open. Cams 70 and 72 taper toward the joint region or junction where each jaw connects with the tubular body 54.

As best seen in FIG. 3, tubular body 54 of intermediate member 16 is preferably formed with jaws 18 and 20 as a single unitary part using a resilient medically-acceptable material such as a spring steel or plastic having suitable elastic properties for normally biasing the upper and lower ones of jaws 18 and 20 apart while permitting jaws 18 and 20 to be moved towards one another in response to axial forces acting on the jaws and/or cams as a result of relative movement between the outer tubular member 14 and intermediate member 16. Referring again to FIG. 2, it can be seen that a bias member 53 is connected between flange 50 of outer tubular member 14 and front wall 30 such that outer member 14 is normally biased in a proximal direction relative to intermediate member 16. Bias member 53 is shown as a helical coil spring disposed around intermediate member 16 and held in compression between flange 50 and front wall 30. However, bias member 53 can be constituted of various other types of springs as well as other types of bias devices including tension springs, torsion springs, pan springs, leaf springs, rubber, plastic or magnets, for example.

As best seen in FIGS. 8 and 9 which illustrate inner member 22 removed from outer member 14 and intermediate member 16 for illustrative purposes, inner member 22 includes a cylindrical or tubular shaft 74 and an operating member in the form a distally extending hook 206. Hook 206 terminates proximally at base plate 208 extending perpendicularly from an end of tubular shaft 74 and includes solid shank 210 extending distally from an edge of base plate 208 to terminate at substantially U-shaped needle 212 having a blunt or sharp tip extending back proximally toward base plate 208. Shank 210 and plate 208 can be fitted within groove 68 extending through jaws 18 and 20 so hook 206 can protrude distally beyond lower jaws 18 and 20 as illustrated in FIG. 10. Also stops can be defined in grooves 68 to limit distal movements of hook 206 as desired. The length of inner member 22 can be adjusted for the desired stroke of movement. Axial movement of tubular shaft 74 within intermediate member 16 advances and retracts hook 206 relative to jaws 18 and 20 so that when jaws 18 and 20 are closed, hook 206 can be used in cooperation with jaws 18 and 20 to capture anatomical tissue T in the region between curved needle 212 and the distal end of the jaws as shown in FIG. 10. Hook 206 can also be configured for use as a cautery or to snag, puncture or manipulate anatomical tissue as desired.

Referring to FIG. 2, tubular shaft 74 is telescopically fitted within tubular body 54 of intermediate member 16 and extends through aligned openings in front and rear walls 30 and 31 and intermediate wall 34 of housing 12 to terminate proximally outside housing 12 at spherical reservoir 84 with proximal aperture 88 and stop cock valve 86 disposed within the reservoir for controlling passage of instruments and/or fluids through aperture 88 and into tubular shaft 74.

Handle 90 extends transversely from tubular shaft 74 near the proximal end of tubular shaft 74 and is angled proximally to form a finger rest. Insulated connector 92 can be provided to permit electrical conductors to enter tubular shaft 74 on a side opposite handle 90 to be connected with electrically conductive elements of instrument 10 for performing unipolar or bipolar electric coagulation, for example using hook 206 or jaws 18 and 20 as a conductive element. Tubular shaft 74 also carries transverse flange 94 disposed within housing 12 between rear wall 31 and intermediate wall 34 (see FIG. 2). Bias member 100, shown as a helical coil spring, is disposed around tubular shaft 74 and held in compression between flange 94 and intermediate wall 34 to bias inner member 22 proximally within housing 12 and intermediate tubular member 16.

Inner member 22 is prevented from being inadvertently moved in a distal direction by safety mechanism 36 similar to that disclosed in the parent application, disposed within housing 12 as shown in FIG. 2. A push-button type of safety mechanism 36 such as that disclosed in detail in the parent application, is shown whereby inner tubular member 22 can be locked in a retracted position with flange 94 abutting rear wall 31 by depressing button 39 and can subsequently be released prior to being moved distally by depressing button 39 a second time. It will be appreciated, however, that other safety mechanisms can be used, including rotatable levers, detents, and splined collars for example. Safety mechanism 36 includes post 37 extending radially through housing 12, bias member 38 connected between post 37 and housing 12 for biasing post 37 radially outward, push-button 39 mounted on top of post 37 externally of housing 12 latch spring 40 disposed within housing 12 for engaging post 37 in a locked position where a lower end of post 37 engages flange 94, and trigger 41 for releasing latch spring 40 to allow post 37 to move radially outward to an unlocked position.

Post 37 is oriented transversely relative to the longitudinal axis of inner member 22 and includes annular flange 42 disposed within housing 12. Bias member 38 is shown as a helical coil spring disposed around post 37 and held in tension between housing 12 and annular flange 42 to bias post 37 radially outward of housing 12. Latch spring 40 is formed of a resilient strip of material configured to have flat base 43 secured to cylindrical wall 28 and downwardly angled arm 44 extending from a proximal end of base 43 toward post 37. Arm 44 bends back on itself to form latching surface 45 that is substantially parallel to annular flange 42. Transverse extension 46 of arm 44 extends from a distal end of latching surface 45 in parallel to post 37. Trigger 41 is disposed proximate arm extension 46 and is pivotally mounted in housing 12. Trigger 41 is generally L-shaped and has leg 49 overlying arm extension 46 and leg 51 extending transversely from leg 49 and at a slight downward angle, to be disposed beneath annular flange 42 when post 37 is in the locked position shown in FIG. 2. A torsion spring (not shown) can be connected between trigger 41 and housing 12 to bias trigger 41 in a counterclockwise direction in FIG. 2 such that leg 49 is normally in contact with the arm extension 46.

Referring still to FIG. 2, it will be seen that movable handle 26 is pivotally mounted on pin 102 secured to mounting plate 103 extending outward from side wall 28 along an edge of slotted opening 48. Fixed handle 24 includes finger loop 104 configured to accommodate one or more fingers, or the thumb, of the surgeon and shank 106 connecting finger loop 104 with mounting plate 102. Movable handle 26 includes finger loop 110 configured to accommodate one or more fingers of the surgeon and shank 112 connecting finger loop 110 with flattened end portion 114 which extends into housing 12 towards flange 50 of outer member 14 through slotted opening 48. Intermediate member 16 is fixed to housing 12 by bracket 116. When movable handle 26 is pressed towards fixed handle 24 by the surgeon, flattened end portion 114 of movable handle 26 presses against flange 50 as movable handle 26 pivots about pivot 102. This causes distal end 52 of outer member 16 to move at least partly over cams 70 and 72 to press jaws 18 and 20 towards one another to the closed position, as illustrated in FIG. 2.

A pair of mating protrusions 152 and 154 are carried at opposed locations on finger loops 104 and 110 respectively to lock handles 24 and 26 together when pressed towards one another a predetermined angular distance corresponding to a desired resultant position of jaws 18 and 20. Mating protrusions 152 and 154 are shown having serrated inside surfaces, but can have any other configuration to ratchet, mate frictionally and/or latch together when engaged. The surgeon's fingers can be placed in the finger loops or wrapped around the finger loops.

Use of endoscopic instrument 10 of the present invention is illustrated in FIGS. 11–17, wherein instrument 10 is shown being guided through portal sleeve 156 positioned in wall W of an anatomical cavity. Instrument 10 is preferably passed through portal sleeve 156 with jaws 18 and 20 at least partly closed so that instrument 10 can be inserted without catching on anatomical tissue or snagging structure within portal sleeve 156. Since outer tubular member 14 can be held by protrusions 152 and 154 in a position partly closing jaws 18 and 20, the surgeon need not exert any force on handles 24 and 26 during insertion.

Figure 11:
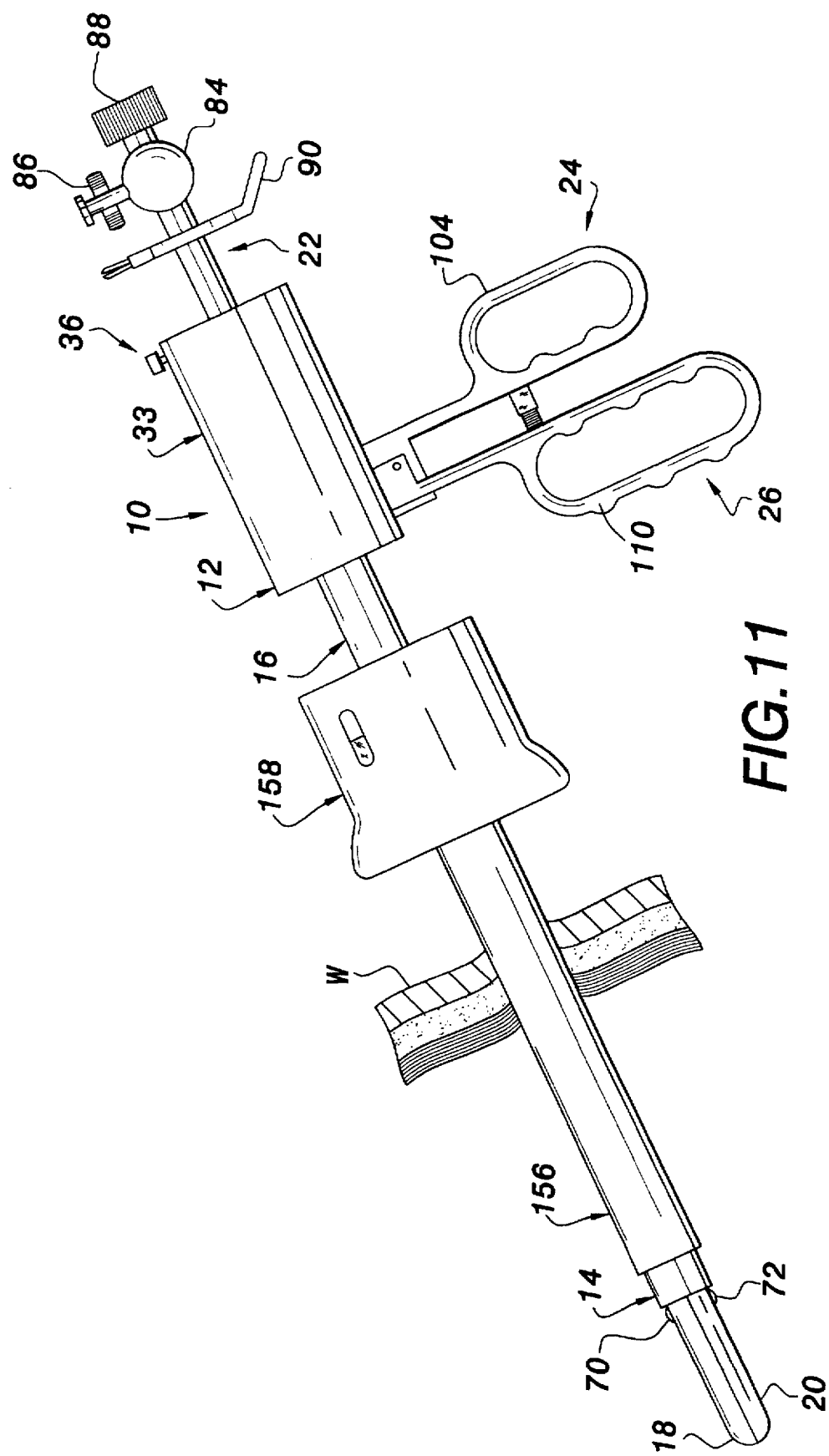
FIG. 11 illustrates the preferred embodiment in use.

With jaws 18 and 20 partly closed, endoscopic instrument 10 is inserted through portal sleeve 156 positioned within the anatomical cavity wall W, as shown in FIG. 11, to access an operative site within the anatomical cavity. Portal sleeve 156 can be positioned in wall W using any suitable penetrating technique, including those creating puncture sites by means of removable obturators such as trocars, and is shown carrying valve housing 158 at a proximal end to prevent the loss of pneumoperitoneum during insertion and withdrawal of endoscopic instrument 10. Visualization of the endoscopic procedure can be accomplished using a conventional endoscope (not shown) incorporated into endoscopic instrument 10, for example within tubular shaft 54, or within an inner member in tubular shaft 54, or separately positioned within the anatomical cavity through a second portal sleeve located at another puncture site.

Figure 12:
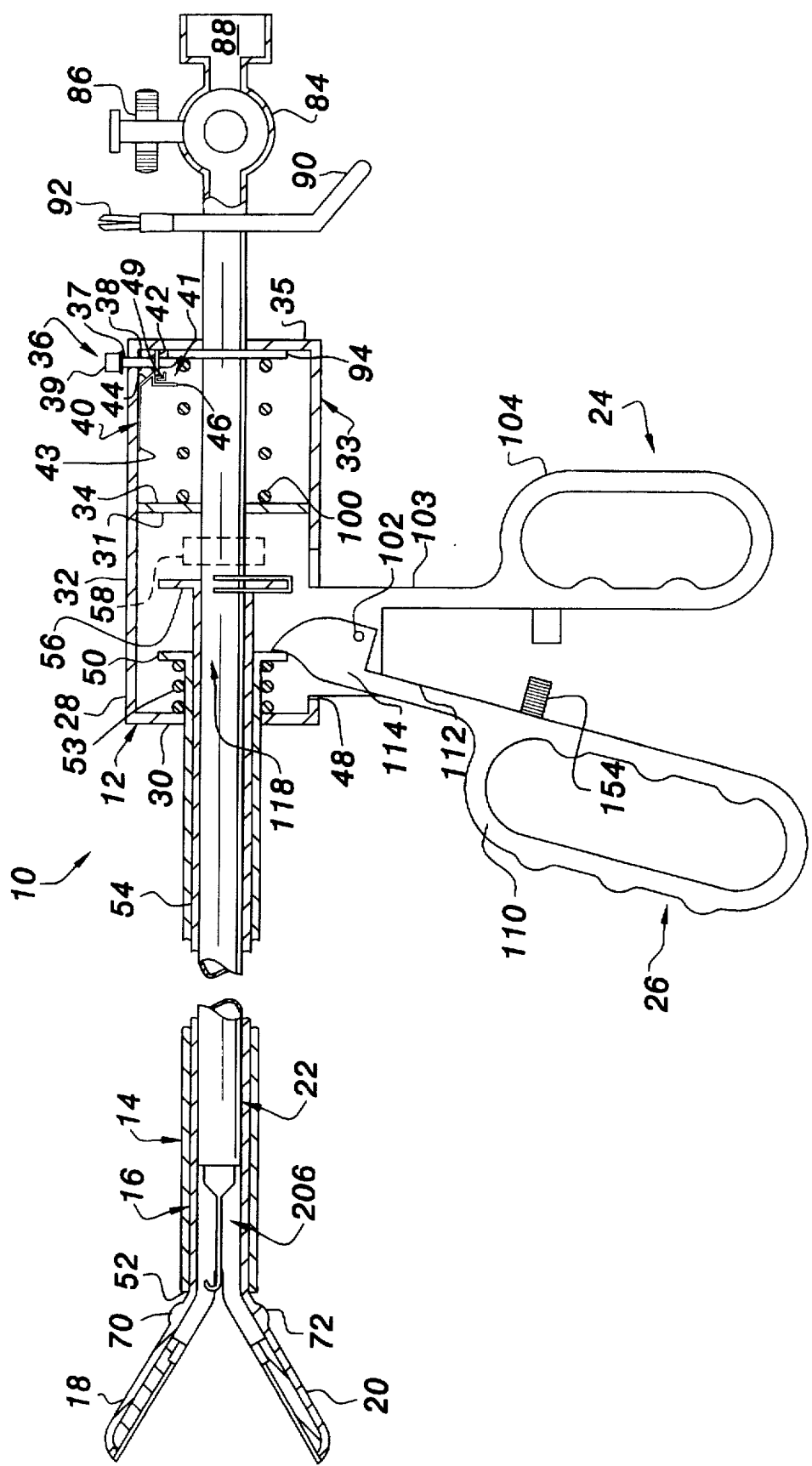
FIG. 12 illustrates the preferred embodiment in cross-section with the jaws open.

Endoscopic instrument 10 is advanced distally through portal sleeve 156 until jaws 18 and 20 emerge into the anatomical cavity. At this point, jaws 18 and 20 can be opened to permit visualization by an endoscope through tubular shaft 54 or can remain closed in the case of using a separately positioned endoscope. If jaws 18 and 20 are to be opened, this is accomplished by exerting finger pressure on finger loops 104 and 110 to release protrusion 152 and 154 to spread finger loops 104 and 110 apart as shown in FIG. 12 due to the force of biasing member 53. Pivotal movement of finger loop 110 about pin 102 allows flange 50 to move proximally with respect to intermediate member 16. This causes distal end 52 of outer member 14 to slide off cams 70 and 72 in a proximal direction allowing jaws 18 and 20 to spread apart elastically, as illustrated in FIG. 12.

Instrument 10 can be moved within the anatomical cavity with jaws 18 and 20 in either the open or closed condition depending on the type of visualization utilized and the desirability of presenting a narrow or wide jaw profile during movement. In FIG. 13, jaws 18 and 20 are shown in the opened condition for being positioned around anatomical tissue T to be grasped. Tissue T is located between inserts 62 and 64 so that when jaws 18 and 20 are partly closed, by placing finger pressure on the handles 24 and 26, tissue T will be held securely within the small gap between jaws 18 and 20 as shown in FIG. 14.

Alternatively, instead of grasping tissue T with jaws 18 and 20, inner member 22 can be advanced distally as shown in FIG. 15 to move hook 206 into an area between open jaws 18 and 20 for manipulating anatomical tissue T. Alternatively, hook 206 can be advanced along grooves 68 with jaws 18 and 20 closed, as shown in FIG. 10. First, safety mechanism 36 is released by pressing down on push-button 39 to cause annular flange 42 formed on post 37 to engage trigger leg 51 rotating the trigger clockwise in FIG. 2. Trigger 41 is spring-biased in a counterclockwise direction and will thus return to its original position once annular flange 42 advances beyond trigger leg 51. When pressure on the push-button 39 is released, safety bias member 38 will draw the post 37 upward in FIG. 2 so that flange 42 will engage trigger leg 51 from the other side causing trigger 41 to rotate counterclockwise and trigger leg 49 to bear against arm extension 46. Arm extension 46, and thus latching surface 45, are moved away from post 37 permitting bias member 38 to move post 37 to its unlocked position shown in FIG. 15 where annular flange 42 abuts outer wall 28 of housing 12.

Figure 17:
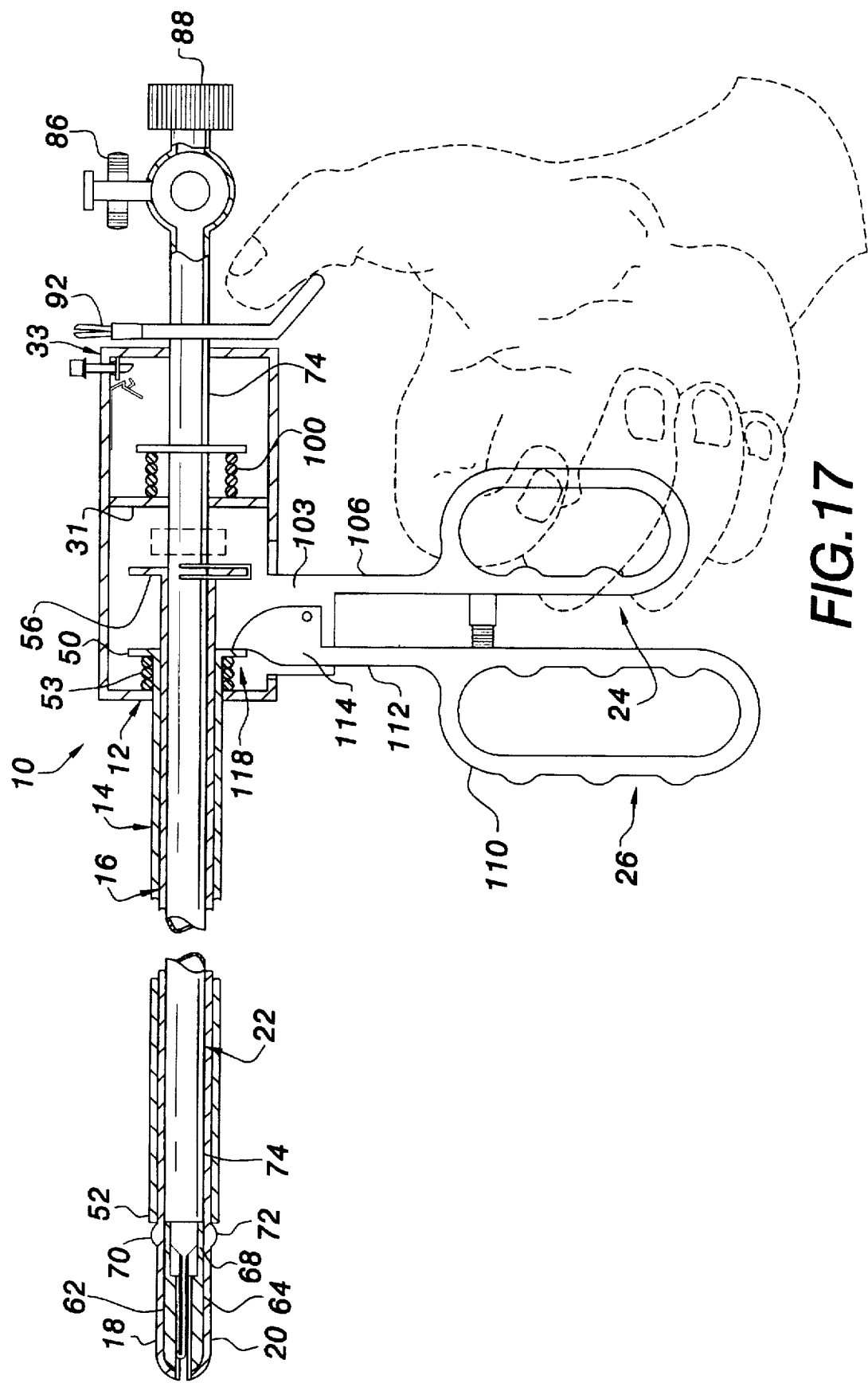
FIG. 17 is a sectional view of the preferred embodiment with the inner member advanced distally.

With safety 39 mechanism disabled, inner member 22 can be advanced by moving handle 90 toward housing 12. Hook 206 at the distal end of inner member 22 is aligned with the grooves 68 formed in jaw inserts 66, for example by use of splines formed along the length of inner member 22, and is slidable along grooves 68. Therefore, hook 206 can move into an area between jaws 18 and 20 as illustrated in FIG. 17. Therefore, hook 206 can move into an area between jaws 18 and 20 as illustrated in FIG. 17. Since grooves 68 in this embodiment extend the entire length of jaws 18, hook 206 can move distally beyond jaws 18 and 20 when jaws 18 and 20 are closed. Of course, in this case, inner member 22 must be of a length sufficient to permit hook 206 to extend beyond jaws 18 and 20. Tissue T can be manipulated, pierced, or cauterized with hook 206 as desired. As mentioned previously, tubular shaft 74 is hollow and can thus be utilized for creating suction during the procedure, performing aspiration or irrigation or to facilitate passage of additional instruments or fluids into the anatomical cavity as desired. After manipulating is completed, hook 206 can be retracted under the influence of bias member 100 or instrument 10 can be withdrawn in its entirety.

Figure 16:
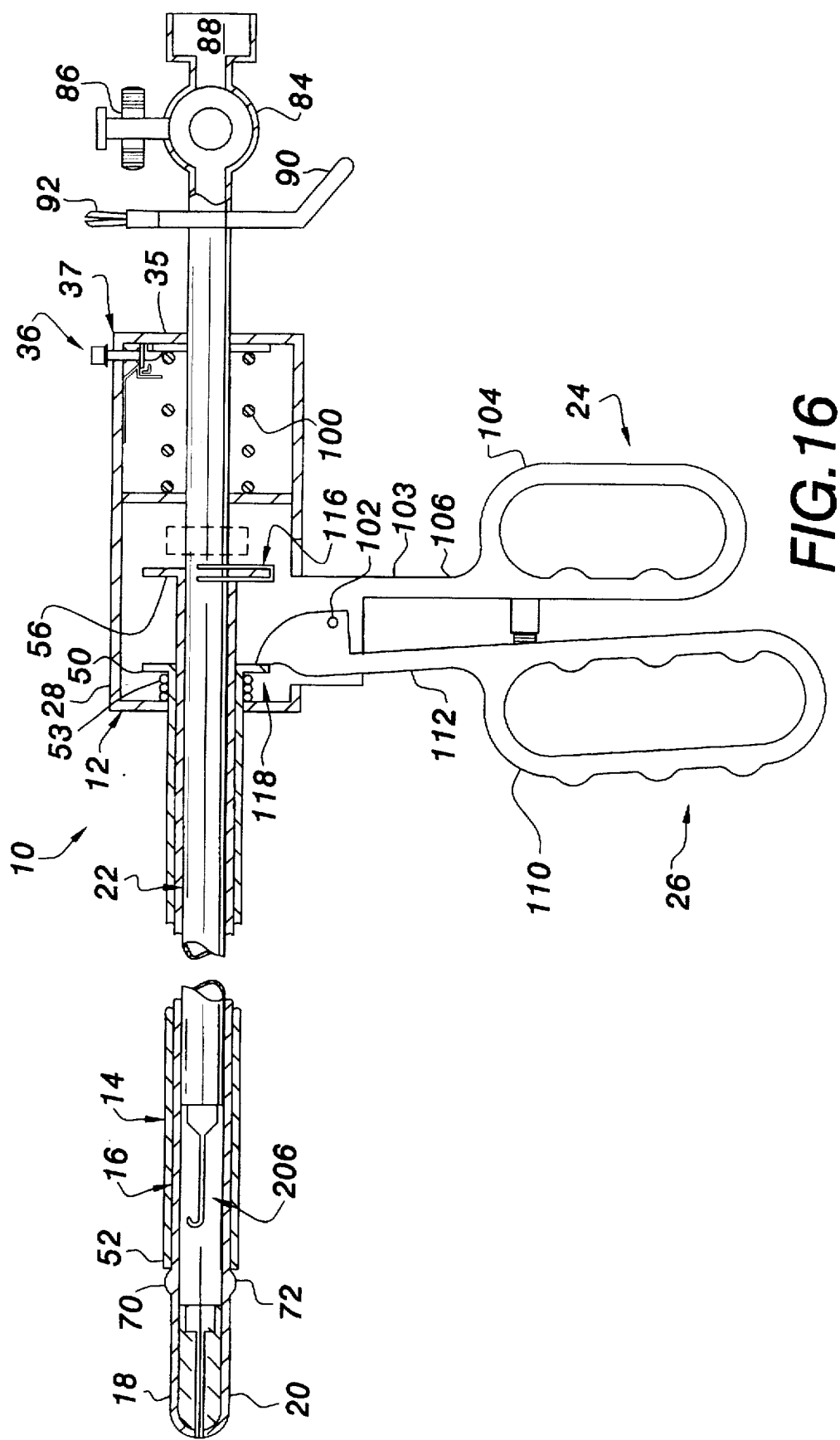
FIG. 16 is a sectional view of the preferred embodiment with the jaws closed entirely.

As mentioned previously, tissue can be grasped and securely held with jaws 18 and 20 in a partly closed state. However, for certain procedures it may be desirable to draw jaws 18 and 20 completely together as shown in FIG. 16, with or without objects held between jaws 18 and 20. Jaws 18 and 20 can be closed completely or clamped together by drawing finger loops 104 and 110 towards one another until distal end 52 of outer member 14 slides further distally over cams 70 and 72 to force jaws 18 and 20 into close contact with one another. If tissue or some other object is disposed between jaws 18 and 20, further advancement of outer member 14 over cams 70 and 72 will result in greater compression of the object. When loop handles 104 and 110 are drawn sufficiently close to one another, mating protrusions 152 and 154 will be engaged, locking handles 24 and 26 in their current position. If mating protrusions 152 and 154 are ratcheted as shown, various degrees of compression can be achieved and maintained without continuous finger pressure being applied.

FIG. 18 shows a modification of the jaws of endoscopic instrument 10 of the preferred embodiment in which jaws 18 and 20 include arcuate or concave portions 160 and 162, respectively, integrally-formed at opposed locations along the length of jaws 18 and 20. Arcuate portions 160 and 162 cooperate to define a substantially circular transverse passage through jaws 18 and 20 when closed and can thus hold a tubular organ, other anatomical tissue or an object therebetween without compressing or flattening the organ, tissue or object. Tissue gripping surfaces 66 are formed on the flat portions of jaws 18 and 20 and can be formed along arcuate portions 160 and 162 as well. Grooves 68 are interrupted by arcuate portions 160 and 162 but extend longitudinally along flat portions of jaws 18 and 20 and are aligned to form a track for guiding hook 206 or other operating members across arcuate portions 160 and 162. When grooves 68 extend the entire length of jaws 18 and 20 as shown, grooves 68 can define an aperture at the distal end of jaws 18 and 20.

Figure 20:
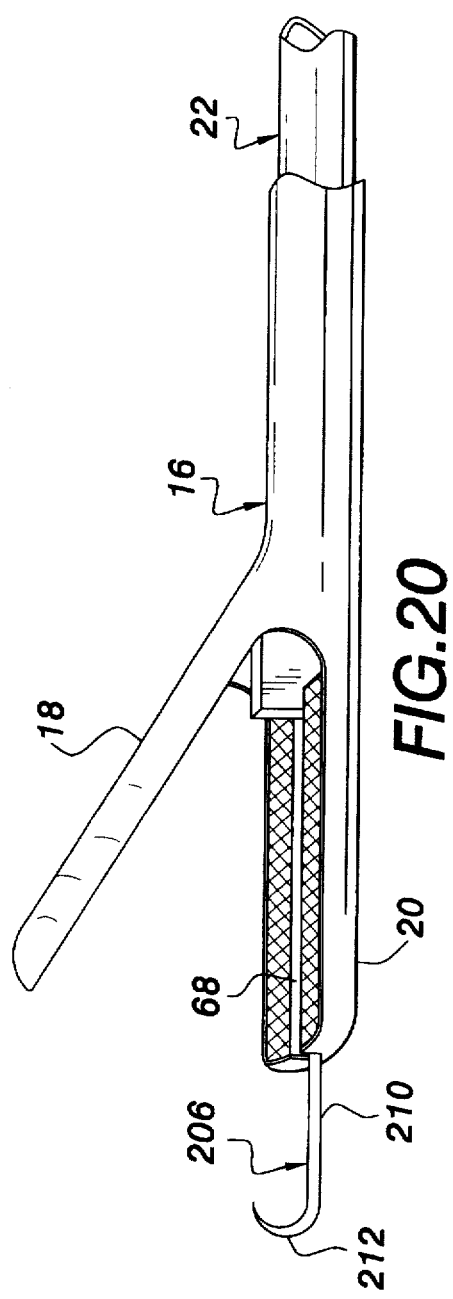
FIG. 20 illustrates the jaw configuration of FIG. 19 with the inner member advanced distally.

In yet another modification of the jaws of the endoscopic instrument 10, shown in FIG. 19, lower jaw 20 is fixed and extends distally from tubular body 54 along a longitudinal axis of tubular body 54. Upper jaw 18 has cam 70 and is movable from an open position normally extending at an angle relative to the longitudinal axis of tubular body 54 to a closed position where it mates with fixed lower jaw 20. Fixed lower jaw 20 can also carry a cam 72. Jaws 18 and 20 include tissue gripping surfaces 66 and grooves 68 formed along the length of the tissue gripping surfaces to serve as a guide for hook 206 and to form a distal aperture as shown in FIG. 20.

Figure 21:
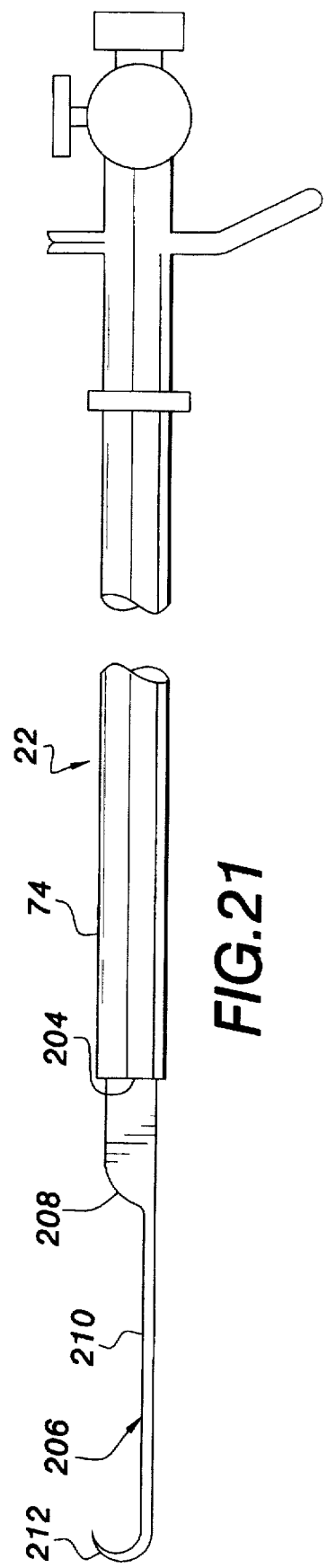
FIG. 21 illustrates the modified inner member of FIG. 20.

Another inner member 22 carrying a solid hook is illustrated in FIG. 21 and is similar to the inner member shown in FIG. 8 with the exception that shank 210 extends from base plate 208 along a longitudinal axis that is offset from the central axis of tubular shaft 74 and the curved needle 212 has a larger radius of curvature to facilitate passage of the needle through intermediate member 16. Shank 210 fits within slot 68 of one of jaws 18 and 20, as shown in FIG. 20, and can be used as a cautery or to snag, capture, puncture or manipulate anatomical tissue depending on the procedure being performed. Inner member 22 of FIG. 21 can be used with any jaw configuration. Tubular shafts 74 of the inner members discussed above have open distal ends for permitting passage of fluids therethrough and base 208 is disposed diametrically across the open distal end. However, the distal end of tubular shafts 74 can be closed.

Inner members 22 shown in FIGS. 22 and 23 are similar to those shown in FIGS. 21 and 8, respectively, but without base plates 208 and with shanks 210 and curved needle portions 212 being hollow. Tubular shaft 74 for each inner member 22 in these figures terminates distally in a front wall 204 and each hollow shank 210 extends distally from an opening in the front wall 204 to terminate at hollow curved hook 212 with aperture 214 at a tip for passage of fluids, such as vasoconstricting medicaments, or lengths of suture material therethrough.

FIG. 24 illustrates another inner member 22 similar to that shown in FIG. 22 but with continuous open channel 216 formed along an inside surface of the shank 210 and needle 212. Fluid passing through a small opening in distal wall 204 proximate channel 216 is directed along channel 216 to form a diffuse flow in the region about channel 216. The inner member 22 shown in FIG. 25 is similar to that shown in FIG. 24 with the exception of tubular shaft 74 having an open distal end 218 for creating an even more diffuse flow or permitting passage of other implements therethrough.

Needle 212 for inner member 22 shown in FIG. 26 is straight and extends perpendicularly from shank 210. A channel is formed inside shank 210 and needles 212 from a small opening in wall 204 at the distal end of tubular shaft 74 to the open tip of needle 212.

Another inner member 22 is illustrated in FIGS. 27 and 28 which includes tubular shaft 74 having an open distal end 218 carrying a perpendicularly angled hook 206. Hook 206 terminates proximally at base plate 208 extending diametrically across open distal end 218 of tubular shaft 74 and includes solid shank 210 extending distally from a lower edge of base plate 208 and terminating at perpendicular needle 212 having opening 213. Inner member 22 shown in FIG. 29 is similar to that shown in FIG. 27 but with a curved, rather than straight, needle 212. Needles 212 for inner members 22 shown in FIGS. 27 and 29 are shown having relatively blunt tips 213 for contacting anatomical tissue without penetrating into the tissue. It will be appreciated, however, that tips 213 can be sharp to penetrate anatomical tissue if desired.

When inner member 22, such as that shown in FIG. 25, has an open distal end 218, implements can be introduced into tubular shaft 74 through aperture 88 and advanced distally to emerge through open distal end 218 of tubular shaft 74. FIG. 30 illustrates an exemplary instrument 220 that can be inserted through tubular shaft 74. Instrument 220 has a tubular body 222 carrying cutting blade 224 at a distal end. Cutting blade 224 includes distal cutting edge 226 configured to fit within channel 216 formed in needle 212 as shown in FIG. 31. In use, inner member 22 can be positioned with needle 212 extending distally from closed jaws 18 and 20 to capture tissue between needle 212 and the distal end of jaws 18 and 20 and tubular implement 220 can be advanced distally through tubular shaft 74 until blade 224 slides along channel 216 to cut the tissue held between needle 212 and jaws 18 and 20. FIG. 32 illustrates a distal end of a modified outer member 14. Slots 15 are formed in the distal end to receive cams 70 and 72 to maintain alignment of jaws 18 and 20.

From the above, it will be appreciated that the endoscopic instrument of the present invention permits multiple functions to be performed endoscopically by use of a forceps unit having a tubular member with jaws configured for grasping or holding objects such as anatomical tissue or needles and an inner member telescopically fitted within the forceps unit tubular member and carrying a hook for performing at least one of the functions of hooking cutting, penetrating, injecting fluids, creating suction, aspirating, irrigating, grasping, manipulating, hooking, dissecting and cauterizing, for example. The tubular member and jaws of the forceps unit are preferably formed as an integral one-piece construction and are movably disposed within an outer member to permit sliding movement of the outer member over the jaws. The outer member and tubular forceps can be mounted on a housing and coupled using any suitable handle mechanism and linkages for producing relative movement between the jaws and the outer tubular member. Because the jaws are carried at the end of a tubular body, the forceps can be positioned within an anatomical cavity with various inner members being advanced distally through the tubular body for performing different functions. The inner member can also have hollow tubular shafts open at a distal end for facilitating visualization with a conventional endoscope, illumination with fiber optics or other suitable light sources, for passage of implements such as blades or ligature appliers to cooperate with instruments mounted at the distal end of the inner member tubular shaft, and/or for introducing or collecting fluids prior to, during or after an operative step, such as cutting or puncturing, is completed. When a tubular shaft is closed at a distal end and a hollow hook extends from an opening in the closed distal end, the inner member can be used for precisely administering medicaments such as vasoconstrictors (e.g., epinephrine) or other fluids to an operative site, or for passing lengths of suture material through the hollow hook to suture tissue within the anatomical cavity.

The jaws of the present invention can be straight, curved and/or angled and can have integrally formed or removable inserts with configurations for grasping and holding tissue and objects such as needles. Note that, while the jaws are discussed generally above as part of forceps, the jaws can be used to grasp a needle or other object for suturing or the like. The inserts can have any combination or number of longitudinal grooves formed in the inserts for accommodating end effectors. The grooves can extend part way to define stops or abutments limiting distal movement of the hook or can extend the complete length of the inserts to form openings or apertures at a distal end of the jaws to allow passage of the hook beyond the distal end of the jaws when the jaws are closed. The jaws can have any shape in cross-section when closed, including circular, elliptical, rectangular and polygonal configurations, and can have opposed arcuate or concave portions for clamping tubular objects without compressing the objects.

Integral blades can be carried by one or both jaws and centrally located for cutting anatomical tissue or can be offset laterally from the central longitudinal axis of the jaws to permit better visualization and the formation of a longitudinal groove for passage of other operating members through the jaws. If a single blade is carried by one jaw, the other jaw can carry an opposed blade in a manner to permit sliding contact with scissor-like cutting, direct abutment of cutting edges to produce a chopping cut, and/or can form a pocket for receiving the cutting edge of the opposed blade to permit partial or complete closure of the jaws together. Furthermore, any blade of a scissor device carried by the jaws or an inner member of the present invention can be provided with a sharp hook extending transversely from the distal end of the blade in opposed relation to the other blade.

When the jaw inserts are removable, the empty cavities defined by the jaws can be used for accommodating cartridges holding surgical staples or clips such that by closing the jaws the staples or clips can be applied to anatomical tissue. Moreover, the elongate tubular structure of the inner member permits a series of cartridges to be carried therein for being applied individually within the anatomical cavity without removal of the inner member.

The position of the electrical connector opposite the handle is merely exemplary of the many various locations at which an electrical connector can be positioned. For example, an electrical connection could be made directly with the housing of the forceps to utilize the jaws or the hook as conductive elements for performing electrosurgery. Also, inner surfaces of any of the tubular members, can be electrically insulated to permit passage of electrosurgical instruments therethrough.

The handles and linkages shown and described herein for sliding the outer member over the jaws are exemplary of the types of handle mechanisms suitable for performing the function of closing the jaws. However, the handles can have any configuration for producing relative movement between the outer and intermediate members, including two pivoted legs with finger loops and sliding brackets as disclosed in the parent application, one fixed and one pivoted leg with finger loops, a pistol grip with a movable trigger, or resilient U-shaped members connected between outer and intermediate members. Moreover, the handles can have any orientation relative to the longitudinal axis of the instrument including, for example, substantially transverse orientations whereby the handles extend transversely from a sidewall of the housing or substantially longitudinal orientations whereby the handles extend longitudinally from a rear wall of the housing and are operated like a scissors or even rotatable configurations whereby the handles can be moved between transverse and longitudinal orientations as desired by being selectively disengaged from the jaws. Suitable linkages include brackets with sliding motion, gears and/or racks mounted on or between handles and the outer and intermediate members, pulleys and cords or any other direct or indirect coupling mechanisms.

The intermediate and outer members can be frictionally fitted to maintain a position by resisting relative movement, can be biased apart with a bias member such as a torsion spring connected between the handles or a helical coil spring disposed around the intermediate member and held in compression between intermediate and outer member flanges, or can be biased together as desired. If the outer tubular member is biased relative to the intermediate member, a mechanism can be provided for releasing/locking the bias member to permit the outer tubular member to be maintained at any position relative to the jaws, for example by frictional engagement.

The components of the endoscopic instrument of the present invention can be made of any suitable, medical grade materials to permit sterilization for re-use or for single patient use. The components can be made of multiple parts of various configurations and materials to reduce cost. The instrument can have various valves, stop cocks and seals to control fluid flow therethrough, such as the valve 58 schematically shown in phantom in FIG. 2. Also, the hook can be removably attached, by a screw thread or the like, to the inner member to permit changing the hook configuration.

The features of the various embodiments described above can be combined in any manner desired dependent upon the operational requirements of the procedure to be performed and the complexity of the endoscopic instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical instrument comprising
   a tubular outer member having a proximal and terminating distally at a distal end;
   an intermediate member having a tubular body disposed telescopically within said outer member, a proximal end and a distal end defining a pair of opposed jaws resiliently biased apart;
   an inner member slidably disposed at least partly within said intermediate member and comprising a shaft and a hook on a distal end of said shaft, said hook comprising a shank and a needle extending transversely from a distal end of said shank; and
   a handle coupled with at least one of said intermediate and outer members and configured to move said pair of opposed jaws between open and closed positions when said distal end of said outer tubular member is moved relative to said jaws.

2. An instrument as recited in claim 1 wherein said jaws define opposed grasping surfaces.

3. An instrument as recited in claim 2 wherein a longitudinal groove is formed in one of said grasping surfaces.

4. An instrument as recited in claim 3 wherein said longitudinal groove extends part way along said one of said grasping surfaces to define a stop limiting distal movement of said hook advanced along said groove.

5. An instrument as recited in claim 3 wherein said longitudinal groove extends along an entire length of said one of said grasping surfaces to define an aperture at a distal end of said jaws.

6. An instrument as recited in claim 2 wherein a longitudinal groove is formed in each of said grasping surfaces.

7. An instrument as recited in claim 6 wherein said longitudinal grooves extend part way along said grasping surfaces to define a pair of stops limiting distal movement of said hook advanced along said grooves.

8. An instrument as recited in claim 6 wherein said longitudinal grooves extend along entire lengths of said grasping surfaces to define an aperture at a distal end of said jaws.

9. An instrument as recited in claim 1 wherein said jaws include opposed arcuate portions defining an opening between said jaws.

10. An instrument as recited in claim 1 wherein one of said jaws is fixed parallel to a longitudinal axis of said intermediate member and the other of said jaws is movable.

11. An instrument as recited in claim 1 wherein said shaft is tubular, said distal end of said shaft is open and said hook is solid.

12. An instrument as recited in claim 1 wherein said shaft is tubular, said distal end of said shaft is closed and said hook is hollow and extends from an opening in said closed distal end of said tubular shaft.

13. An instrument as recited in claim 1 wherein a channel is formed along a length of said hook.

14. An instrument as recited in claim 13 wherein said shaft is tubular and further comprising an implement telescopically fitted within said shaft and carrying a cutting blade at a distal end for sliding along said channel.

15. An instrument as recited in claim 1 wherein a groove is formed in at least one of said jaws and said hook is configured to slide along said groove when said jaws are closed.

16. An instrument as recited in claim 14 wherein said cutting blade has a curved distal cutting edge configured to conform to the shape of said hook.

17. An instrument as recited in claim 1 further comprising safety means for locking said inner member to prevent movement of said inner member relative to said intermediate member.

18. An instrument as recited in claim 1 wherein said inner member includes valve means at a proximal end for controlling passage through said inner member.

19. A method of performing surgical procedures comprising the steps of introducing a tubular member with jaws through an opening in an anatomical cavity wall;

grasping anatomical tissue with the jaws;

opening the jaws to release the anatomical tissue;

advancing an inner member having a hook distally through the tubular member; and performing a medical procedure with the inner member.

20. A method as recited in claim 19 wherein said performing step includes the step of using said inner member to perform at least one of the functions of cutting, cauterizing, penetrating, injecting, grasping, manipulating, hooking, creating suction, dissecting, irrigating and aspirating.

21. A method as recited in claim 19 wherein said introducing step includes closing said jaws by sliding a tubular outer member over said jaws.

22. A method as recited in claim 21 wherein said grasping step includes sliding the outer tubular member proximally with respect to said jaws to permit the jaws to resiliently separate, positioning the anatomical tissue between the jaws and sliding the outer member distally with respect to the jaws to close said jaws around the anatomical tissue.

23. A method of performing surgical procedures comprising the steps of introducing a tubular member with jaws through an opening in an anatomical cavity wall;

advancing an inner member carrying a hook distally through the tubular member until the hook protrudes distally from the jaws; and performing a medical procedure with said inner member.

24. A method as recited in claim 23 wherein said performing step includes using the hook to perform at least one of the functions of cutting, cauterizing, penetrating, injecting, hooking, grasping, dissecting, manipulating, creating suction, irrigating and aspirating.

25. A method as recited in claim 23 wherein said introducing step includes closing the jaws by sliding a tubular outer member distally with respect to said jaws and said advancing step includes moving the hook along a groove formed in the jaws.

26. A method as recited in claim 23 wherein said introducing step includes closing the jaws by sliding a tubular outer member proximally with respect to said jaws and said advancing step includes the step of moving the hook along a groove formed in the jaws.

27. A method as recited in claim 23, further comprising the steps of:

maintaining the jaws in a closed condition, positioning anatomical tissue between the hook and the jaws and retracting the hook in a proximal direction to hold the anatomical tissue between the hook and the jaws.

28. A method as recited in claim 27, further comprising the step of:

advancing a cutting blade through the inner member to slide along a channel formed in the hook and cutting the anatomical tissue held between the hook and the jaws.

29. A surgical instrument comprising a tubular outer member having a proximal end and a distal end, a channel being defined through said outer member;

an intermediate member having a body disposed at least partly within said outer member, a proximal end and a distal end having a pair of opposed jaws;

an inner member slidably disposed at least partly within said channel and comprising a shaft and a hook on a distal end of said shaft, said hook comprising a shank and a needle extending transversely from a distal end of said shank; and a handle coupled with at least one of said jaws and configured to move said jaws between open and closed positions.

30. An instrument as recited in claim 29 wherein said intermediate member passes through said channel and a passage is defined through said intermediate member.

* * * * *